United States Patent
Tsai et al.

(10) Patent No.: US 8,303,554 B2
(45) Date of Patent: Nov. 6, 2012

(54) ASPIRATION SYSTEM AND BODY INTERFACE DEVICE FOR REMOVING URINE DISCHARGED BY THE HUMAN BODY

(75) Inventors: Mingliang Lawrence Tsai, Holmdel, NJ (US); Tinh Nguyen-DeMary, Milltown, NJ (US)

(73) Assignee: ConvaTec Technologies, Inc., Las Vegas, NV (US)

( * ) Notice: Subject to any disclaimer, the term of this patent is extended or adjusted under 35 U.S.C. 154(b) by 384 days.

(21) Appl. No.: 12/738,348

(22) PCT Filed: Oct. 20, 2008

(86) PCT No.: PCT/US2008/080510
§ 371 (c)(1),
(2), (4) Date: Apr. 16, 2010

(87) PCT Pub. No.: WO2009/052502
PCT Pub. Date: Apr. 23, 2009

(65) Prior Publication Data
US 2010/0234820 A1    Sep. 16, 2010

Related U.S. Application Data

(60) Provisional application No. 60/980,908, filed on Oct. 18, 2007.

(51) Int. Cl.
*A61M 1/00* (2006.01)
*A61F 5/44* (2006.01)
*A47K 11/00* (2006.01)

(52) U.S. Cl. ........ 604/319; 604/317; 604/318; 604/327; 604/329; 604/347

(58) Field of Classification Search ............... 73/204.22; 340/693.12
See application file for complete search history.

(56) References Cited

U.S. PATENT DOCUMENTS

| | | | |
|---|---|---|---|
| 3,948,098 A | 4/1976 | Richardson et al. | |
| 4,610,675 A * | 9/1986 | Triunfol | 604/329 |
| 4,631,061 A | 12/1986 | Martin | |
| 5,002,541 A | 3/1991 | Conkling et al. | |
| 6,238,378 B1 * | 5/2001 | Perez | 604/317 |
| 6,706,027 B2 * | 3/2004 | Harvie | 604/347 |
| 6,740,066 B2 | 5/2004 | Wolff | |
| 2004/0236292 A1 * | 11/2004 | Tazoe et al. | 604/317 |
| 2005/0070862 A1 * | 3/2005 | Tazoe et al. | 604/327 |
| 2006/0015080 A1 | 1/2006 | Mahnensmith | |

* cited by examiner

*Primary Examiner* — Jackie Ho
*Assistant Examiner* — Andrew S Lo
(74) *Attorney, Agent, or Firm* — Stuart E. Krieger (57) ABSTRACT

A body interface device for a urine aspiration system comprises a skin contact pad with gel adhesive for adhering to the skin, and a flexible cover attached to the pad. The pad includes at least one aperture for admitting urine through the pad into the body interface device. The flexible cover has a bulged form projecting away from the gasket. The flexible cover defines a urine receiving chamber facing towards the gasket, and recess facing away from the chamber for receiving at least a portion of a non-contact liquid sensor. The recess and chamber have a wall portion in common that separates the recess and the chamber. A liquid acquisition material in the chamber receives and transports urine for rapid sensing by the non-contact sensor. An aspiration unit is responsive to the non-contact liquid sensor to apply aspiration suction to the body interface device, upon detection of urine.

29 Claims, 5 Drawing Sheets

ASPIRATION SYSTEM AND BODY INTERFACE DEVICE FOR REMOVING URINE DISCHARGED BY THE HUMAN BODY

FIELD OF THE INVENTION

The present invention relates to the field of aspiration to remove urine discharged by the human body. In particular, the invention relates to a body interface device for such an aspiration system.

BACKGROUND TO THE INVENTION

Urinary management is of critical need in the acute and long term care settings. Urinary issues are generally grouped into two primary categories: failure to drain; and failure to contain. In the case of failure to drain, the patient cannot spontaneously drain urine from the bladder. The general solution to this problem is to catheterize the patient. In the case of failure to contain, the patient cannot contain the urine within their body until a convenient and expedient time. When patients are not conscious or cognizant, they are typically catheterized. Patients who are aware but non-ambulatory often utilize a manual collector for assistance, such as a bedpan, a male urinal, or an adult diaper. These can be cumbersome to use, and sometimes result in spills on or around the patient. Also, such manual collectors may require frequent changes, placing additional burden on caregivers. When it is desired to monitor the urine output, very often medical staff catheterize a patient even when catheterization is not otherwise required. Catheterization provides a means by which urine can be monitored more easily than with a manual collector.

There is a growing problem with nosocomial infections and a high incidence of catheter-related urinary tract infections (UTIs). Catheter associated UTI is the most common nosocomial infection in hospitals and nursing homes, accounting for up to 40% of all institutionally acquired infections, or more than 1 million infections in U.S. hospitals each year. There is considerable pressure on the healthcare and nursing profession to reduce such infection.

U.S. Pat. Nos. 5,002,541, 4,747,166 and 4,631,061 describe human urine aspiration systems. The urine aspiration systems include an electric pump for applying suction to a urinal. The urinal includes a liquid sensor for automatically activating the pump when the presence of liquid urine is detected. The three patents all describe liquid-contact sensors in the form of electrodes forming a normally open circuit that is closed by electrical conduction through liquid, when the sensor is contacted by liquid. However, there are obvious concerns about the possibility of electrical current leaking from the electrodes, through the conductive urine, to the skin. Moreover, the sensor is necessarily used in close proximity to the sensitive genital area, increasing the concerns of leakage of current that is applied by the electrodes.

The last mentioned patent, U.S. Pat. No. 4,631,061, also suggests the possibility of using at least one pair of optical elements, formed by opposed optical fibers integrated into the liquid passage of the urinal or collection tube to sense the liquid. This is said to avoid electrical currents applied to the urinal. However, the design is very expensive and impractical commercially. It requires at least one pair of optical elements that are optically aligned in a pad with a beam of light passing between the pair of optical elements to sense the presence of liquid. It also needs an optically transparent window to allow the beam of light to pass through. Any residues or moisture condensation could easily cloud the window and falsely trigger the pump to turn on. The optical fibers are expensive items, and integrating these into the urinal or tubing increases the cost of the urinal or tubing, which are preferably disposable for hygiene reasons. Moreover, the electro-optic part is remote from the urinal, and has to be connected by delicate and expensive optical fibers, making the system delicate and expensive as a whole.

A further issue is a design of a body interface device that is comfortable and discrete to wear, yet also provides secure protection against leakage of discharged urine, and allows rapid sensing of urine discharge. The difficulty is especially apparent in devices for female wearers. Achieving a reliable seal around the female genital area is difficult, especially in a device that is conformable so as to be comfortable. Moreover, if a urine discharge is not sensed quickly and reliably, urine may leak as a result of overspillage. This problem is exacerbated if the device is intended to be compact, as there is then little volume in the body interface device to accommodate initial urine discharge.

It would be desirable to improve on prior art designs of aspirated liquid removal systems, especially in terms of urine detection and body interface devices, in order to satisfy commercial need and improve customer acceptance.

SUMMARY OF THE INVENTION

One aspect of the invention provides a body interface device for a urine aspiration system. The body interface device comprises an adhesive pad (also referred to herein as a gasket) for contacting skin, and a cover attached to the gasket.

Optionally, the adhesive pad comprises or carries gel adhesive for adhering to skin. The gasket includes at least one aperture for admitting urine through the gasket into the body interface device.

The cover has a bulged form projecting away from the pad, and defining a profile height of the device. The cover defines a urine receiving chamber facing towards the gasket. Optionally, the cover defines a recess facing away from the chamber for receiving at least a portion of a non-contact liquid sensor. The recess and the chamber have a wall portion in common that separates the recess and the chamber. The distance between the wall portion and the mouth of the urine receiving chamber is smaller than the profile height.

Optionally, a liquid acquisition material is provided within the chamber. The liquid acquisition material provides distribution or wicking of the urine to enable reliable sensing by the liquid sensor.

Optionally, the cover is flexible, and has a thermo-formed three-dimensional shape.

Features and advantages of the invention include providing a body interface device that is one or more of (i) compact, (ii) comfortable to wear, (iii) provides a secure seal against skin (even hairy skin) to prevent leakage or spillage of urine, (iv) is not painful upon removal (even from hairy skin), (v) has a low profile shape, (vi) solves the conflicting requirements for a device especially for a female wearer, (vii) facilitates the possibility of a re-usable liquid sensor, (viii) provides positive positioning of the sensor, (ix) protects the sensor against accidental displacement, (x) provides rapid detection of liquid.

While certain aspects, features and advantages of the invention have been defined above and in the appended claims, claim protection may be sought for any novel feature or idea described herein and/or illustrated in the drawings, whether or not emphasis has been placed thereon.

DETAILED DESCRIPTION OF PREFERRED EMBODIMENTS

Preferred embodiments of the invention are now described with reference to the drawings. The same reference numerals are used to depict the same or equivalent features in each embodiment.

Figure 1:
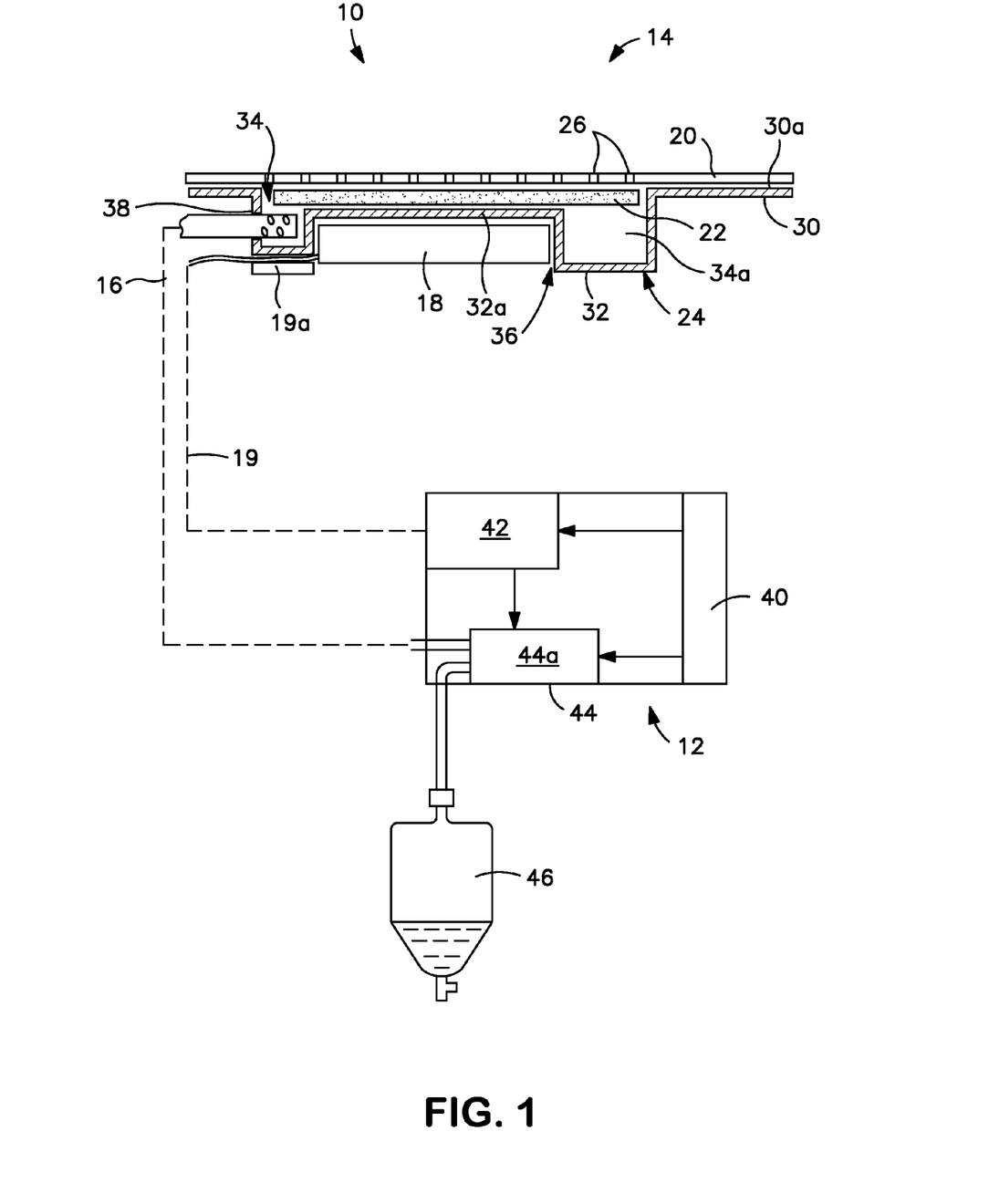
FIG. 1 is a schematic block diagram of a first embodiment of aspiration system for collecting and removing urine, and showing a body interface device in enlarged cross-section.
Figure 2:
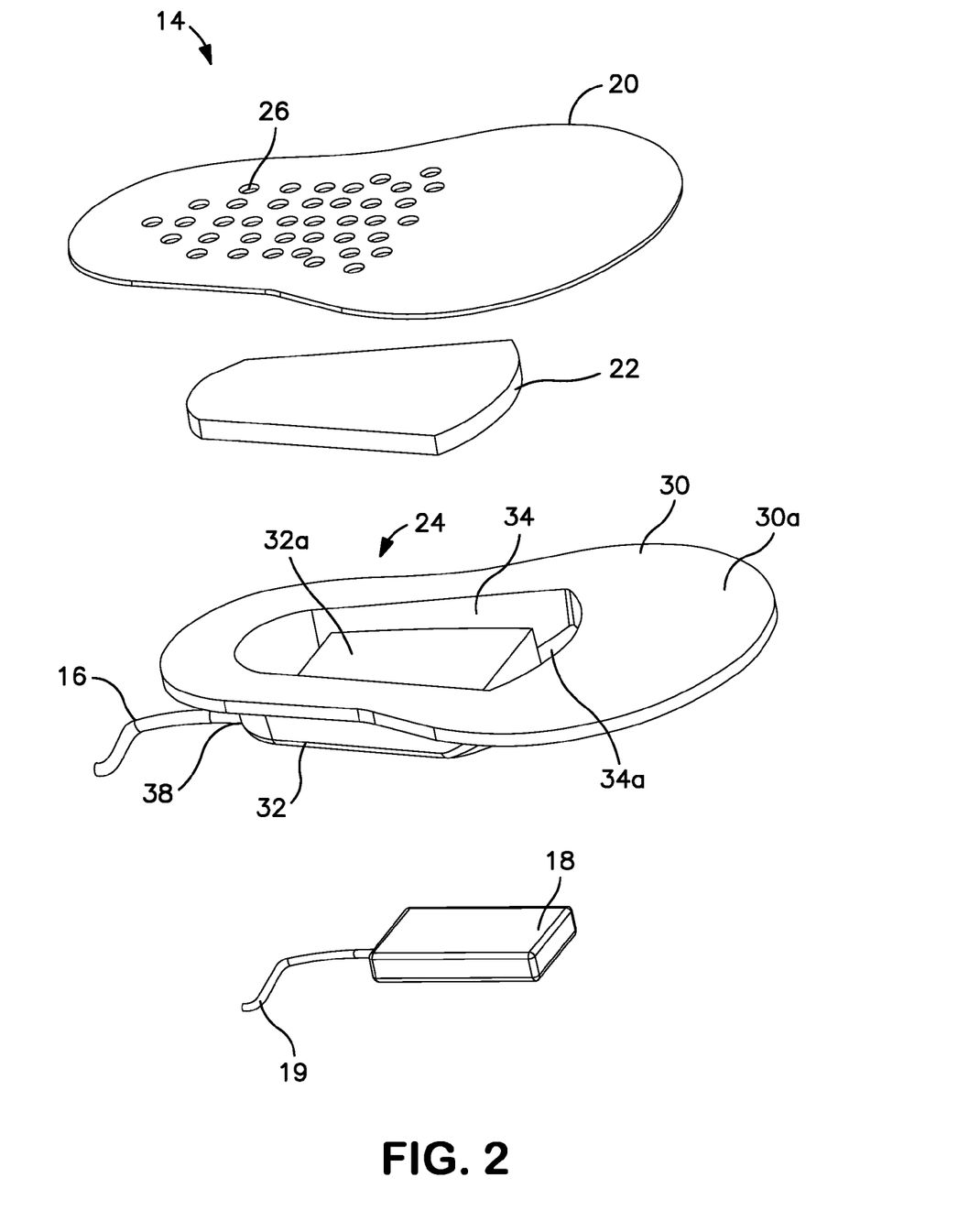
FIG. 2 is a schematic exploded view in perspective from above, showing the components of the body interface device of the first embodiment.
Figure 3:
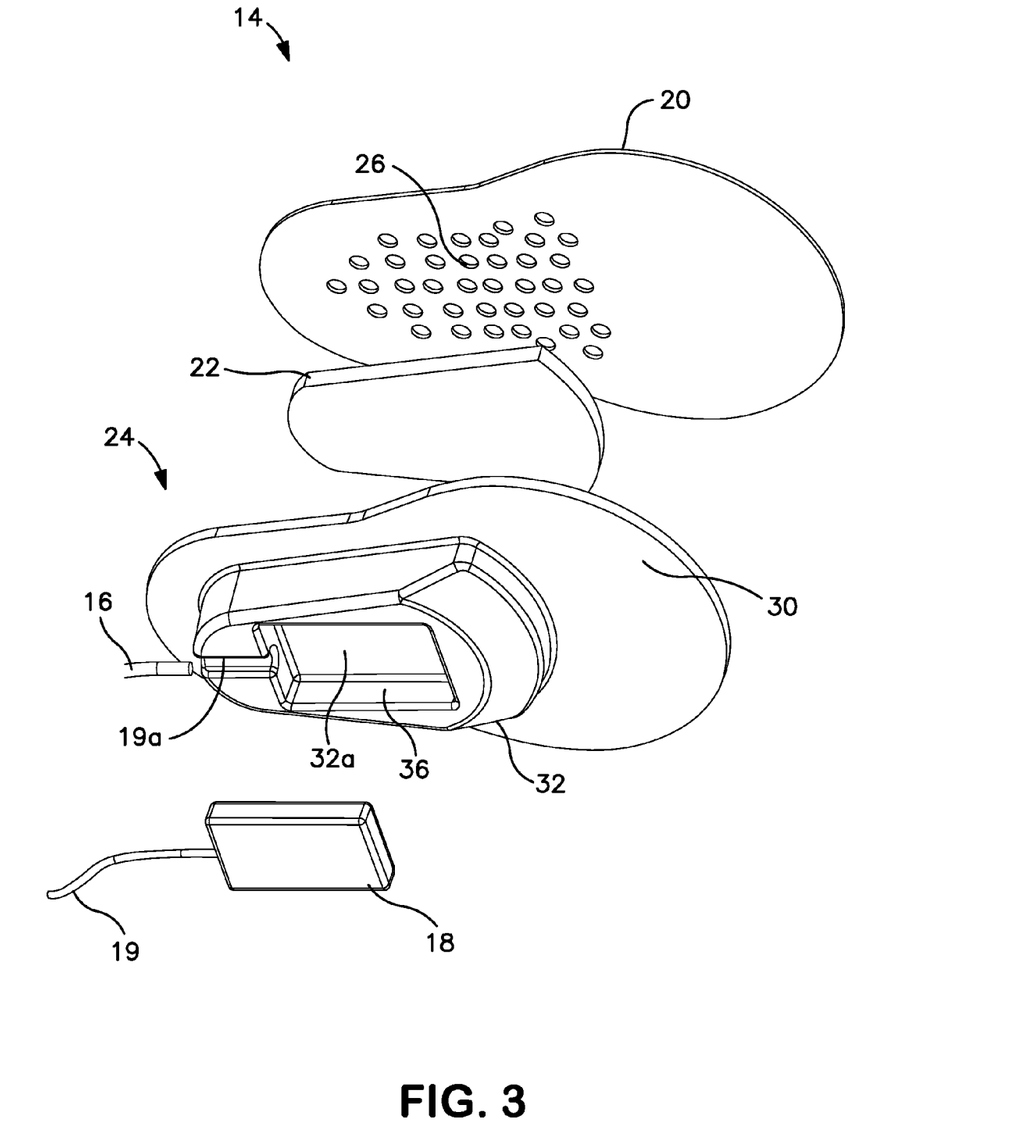
FIG. 3 is a schematic exploded view in perspective from below, showing the components of the body interface device of the first embodiment.
Figure 4:
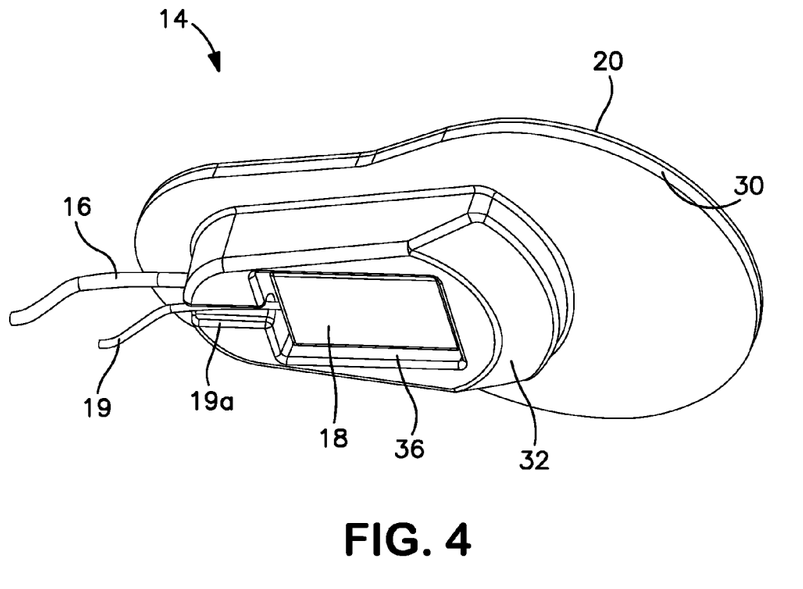
FIG. 4 is a schematic underside perspective view of the body interface device of the first embodiment.
Figure 5:
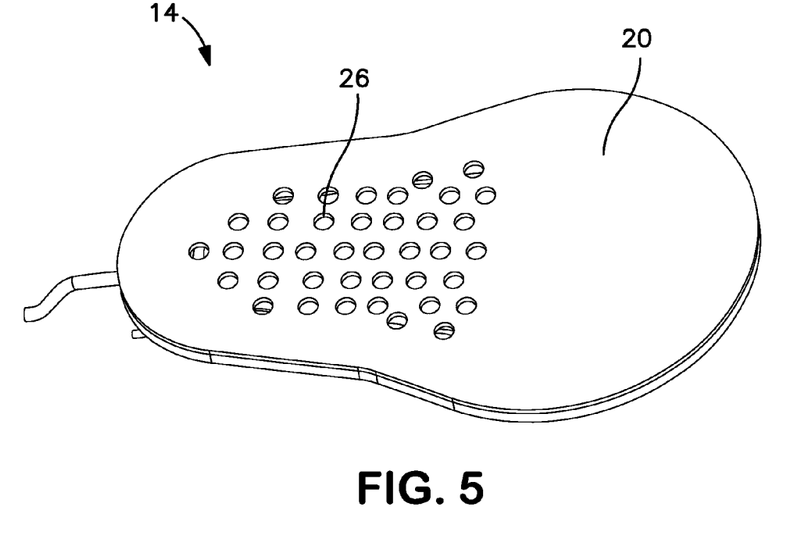
FIG. 5 is a schematic perspective view from above, showing the body interface device of the first embodiment.
Figure 6:
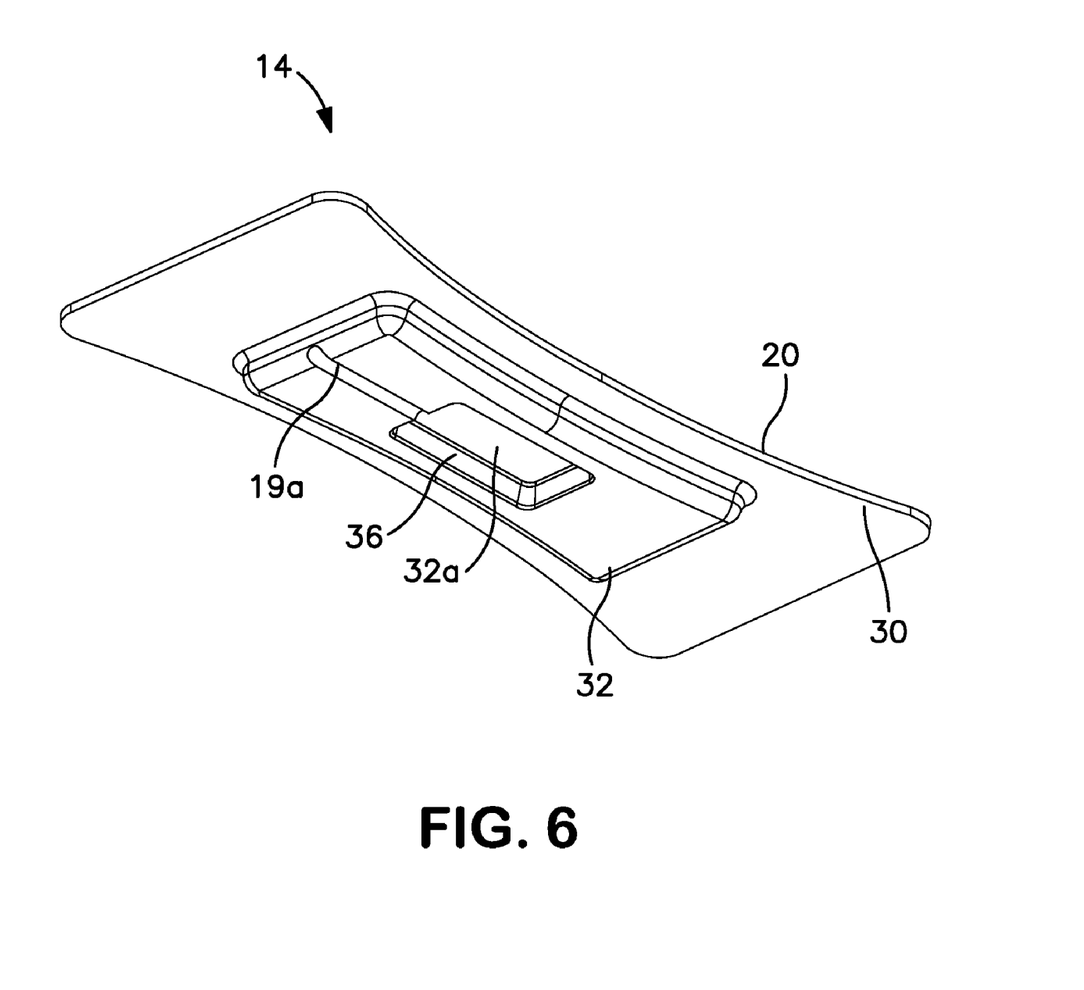
FIG. 6 is an underside perspective view of a body interface device of a second embodiment (and without the sensor in position).

Referring to FIG. 1, an aspiration system 10 for removing urine discharged by the human body generally comprises an aspiration unit 12 and a body interface device 14 coupled to the aspiration unit 12 by means of a flexible conduit 16. The flexible conduit 16 may be regarded as part of the aspiration unit 12 and/or part of the body interface device 14. The body interface device 14 is configured to fit at the genital region of a male or female wearer, or a surgical urostomy. For females, the body interface device 14 is in the form of a snug-fitting urinal (as illustrated). For males, the body interface device 14 is in the form of a male urinal or a condom (not illustrated). For urostomates, the body interface device 14 is in the form of a stoma fitment (not illustrated). The present embodiment is especially suitable for removing urine, since urine removal is most challenging in terms of the volume of the liquid to be removed and the speed of liquid discharge as a surge. This can distance the field of urine removal from other liquid collection systems. The speed of response of the aspiration system 10 to detect and remove the liquid is a significant factor in the ability of the aspiration system 10 to manage a urine discharge, without risk of the urine overflowing from the body interface device 14. Good speed of response enables the size of the body interface device 14 to be reduced to a volume significantly less than that required to contain an entire discharge of urine, providing the possibility of a compact form that can be worn comfortably and discretely. Also, there are significant challenges in terms of cost versus hygiene of the aspiration system 10, as well as profile height of the body interface device 14.

The body interface device 14 for a female wearer is shown in more detail in FIGS. 2-6. The description focuses on the version of the body interface device 14 for a female, as this presents the greater problems in terms of comfort, compact and discrete size, security of a liquid-tight seal preventing over-spillage and general leakage of discharged urine, and rapid detection of a urine discharge. The body interface device 14 generally comprises an adhesive pad (also referred to herein as a gasket) 20, liquid acquisition material 22 (also referred to as liquid handling layer), and a flexible cover 24.

The adhesive gasket 20 is made of or carries a gel adhesive for securing the body interface device 14 to the skin. The gel adhesive has one or more of the following properties:
  (a) The adhesive comprises one or more of a thermoplastic elastomer (TPE), polyurethane, hydrogel, silicone, acrylic, hydrocolloid, etc.
  (b) The adhesive has (i) a skin tack of at least about 300 grams and/or (ii) an adhesive strength of at least 0.2N/in. and preferably at least 0.5N/in. and/or (iii) a relatively low peel strength, i.e., less than about 5N/in., and preferably less than about 3N/in. Such characteristics provide (i) ease of application, and secure attachment of the body interface to the skin, and/or (ii) relatively painless removal (especially from hairy skin).
  (c) The thickness of the adhesive is at least 2 mils, and preferably greater than 20 mils. Such a thickness can provide a good adhesive seal through hair.

In one form, the gasket 20 may be made substantially entirely of the gel adhesive, or it may include the gel adhesive as part of a homogeneous mass. Alternatively, the gasket 20 may comprises a substrate (such as a foam member) carrying the gel adhesive.

The gasket 20 is shaped to form an intimate fit to the skin around the female genital region. In the form shown in FIGS. 2-5, the gasket 20 has a pear shape, optionally slightly elongated. In the alternative form shown in FIG. 6, the gasket 20 has a boat or bow shape that is commonly used in female sanitary pads. In either form, wings (not shown) can also be added, as is known for female sanitary pads. Other shapes of gasket 20 could also be used instead as desired.

The gasket 20 includes one or more open areas 26 for permitting passage of urine through the gasket 20 and into the body interface device 14. In the illustrated female form, the open areas 26 are defined by plural apertures or perforations, such that the gasket 20 has a perforated surface that extends across the female genital area in use. In another form, the open area 26 could be formed by one or more larger apertures, for example, a single aperture.

The flexible cover 24 includes a projecting housing portion 32 defining (i) a urine receiving chamber (or liquid collection chamber region) 34 open towards the gasket 20, and (ii) a sensor recess 36 open in a direction facing away from the chamber 34, for example, in an opposite direction to the gasket 20. The sensor recess 36 is nested within the periphery of the receiving chamber 34, and is defined by a recessed or re-entrant wall portion 32a. The wall portion 32a is common to the receiving chamber 34 and the sensor recess 36, and defines a liquid-tight barrier separating the two. The wall portion 32a has a cup or well shape that defines an island portion around which extends a trough or moat portion 34a of the receiving chamber 34. In the illustrated form, the trough portion 34a extends all of the way around the wall portion 32a, but in an alternative form, the trough portion 34a may extend only part of the way around, making the island portion a peninsular portion.

The depth of the sensor recess 36 is less than the largest depth of the receiving chamber 34. Optionally, the depth of the sensor recess 36 may be not more than 50%, more preferably not more than 40%, more preferably not more than 30% of the depth of the height of the receiving chamber 34 and/or of the profile height of the cover 24.

An outlet port 38 in the wall of the housing portion 32 provides a communication passage for aspiration of urine from the receiving chamber 34. The outlet port 38 may be positioned to communication with the trough portion 34a of the receiving chamber 34 that is co-planar with the sensor recess 36. The flexible conduit 16 connects to, or passes within, the outlet port 38. For example, the portion of the flexible conduit 16 extending into the receiving chamber 34 may be perforated to collect urine. Apart from the outlet port 38, the housing portion 32 may be generally liquid-tight. There is no liquid communication between the receiving chamber 34 and the sensor recess 36.

The sensor recess 36 accommodates, at least partly, a non-contact liquid sensor 18 for detecting, through the wall portion 32a, the presence of urine within the receiving chamber 34. The output from the liquid sensor 18 is used to control operation of the aspiration unit 12 as described later below. The positioning of the liquid sensor 18 within the sensor recess 36 enables a low profile to be achieved, even though the sensor 18 is outside the liquid collection chamber 34. The sensor recess 36 may also provide a large interface area through which the sensor 18 can detect the presence of liquid. The sensor recess 36 also locates the sensor 18 positively, and protects the sensor 18 from accidental displacement during use of the body interface device 14.

The tube 16 enters the flexible cover 24 through the outlet port 38, and can sit behind or inside of the liquid acquisition material 22. This tube 16 can be short to allow the urine to be pumped away from the body interface device 14 and the chamber 34. Optionally, the tube 16 inside of the flexible cover 24 can be long enough to communicate with a large portion of liquid acquisition material 22. The portion of the tube 16 inside of the flexible cover 24 and the chamber 34 can be perforated such that it is effective to convey urine away from the flexible cover 24 and the chamber 34 quickly.

The flexible cover 24 optionally includes a flange portion 30 from which the housing portion 32 projects. The flange portion 30 provides a face 30a for sealing to the gasket 20 around the open area(s) 26, to define a liquid-tight seal. In the present form, the face 30a is engaged adhesively by gasket 20, but in other forms a separate or additional seal may be formed.

The flexible cover 24 is made of generally soft and/or flexible plastics, with a predetermined three-dimensional shape. The shape may be thermoformed in the plastics material. The flexible cover 24 may be made of polyolefin sheets or foams that can be further thermo-formed into the desired geometrical shape. The flexible cover 24 is preferably relatively small such that it can easily be accommodated in the female genital area. For example, the cover 24 may have or cover an area of 120 $cm^2$ or less, preferably 70 $cm^2$ or less.

It is preferred that the housing portion 32 be integrally formed from a single material. However, if desired, one or more regions, for example, the wall portion 32a, may be made as a separate part (optionally of different material or different material properties) that is attached to, or integrated with, the remainder of the housing portion 32.

The liquid acquisition material 22 is disposed within the chamber 34, to extend over the wall portion 32a of the housing portion 32. A function of the liquid acquisition material 22 is to ensure that at least some of the urine entering the chamber 34 is guided, directed and/or transported in front of the sensor recess 36 containing the sensor 18. This can provide rapid and efficient detection of urine, even before the urine begins to fill the trough portion 34a. The liquid acquisition material 22 provides a wicking property, preferably in both horizontal and vertical directions. A typical material includes one or more of: bonded PET fiber fleece; needled punched non-woven; cellulose fibers. The liquid acquisition material 22 is preferred to be hydrophobic so that the material remains relatively dry once aspiration suction is applied to remove the urine from the receiving chamber 34. Such a feature may promote the interior environment of the cover 24 remaining relatively dry, thereby minimizing leakage concern and bacterial growth (e.g., yeast infection).

It will be appreciated from the foregoing that the design of the body interface device 14 enables achievement of the hitherto conflicting requirements of wearer comfort, compact design, low profile with a non-contact sensor, rapid detection of urine, and secure sealing against skin to prevent urine spillage out of the device.

The feature of the liquid sensor 18 being a non-contact sensor provides significant advantages because: (i) the non-contact approach automatically avoids concerns about passing an electrical current through urine in contact with the sensitive genital region of the skin. Instead, there is no direct contact between the liquid sensor 18 and the urine; (ii) the non-contact approach means that the liquid sensor 18 is not contaminated by touching the urine. This allows the liquid sensor 18 easily to be reused with a different body interface device 14; and (iii) the non-contact approach means that the liquid sensor 18 does not itself have to be in a sterile condition before use, thus avoiding the difficulty of, or risk of damage when, sterilizing the aspiration system 10 that does interface intimately with the body.

Optionally, the liquid sensor 18 is separate from, or at least separable from, the body interface device 14. The body interface device 14 is a disposable item that may be manufactured inexpensively, and disposed of after a single use, or a limited number of uses, according to the specific body interface device 14. The liquid sensor 18 may be more expensive, and intended to be used plural times, preferably, with a sequence of different body interface devices 14. This enables the aspiration system 10 to be produced and used very cost efficiently, since the disposable components are generally low cost. The higher cost components may be used multiple times, and may require infrequent replacement. In one form, the liquid sensor 18 is a universal device that may be used with any of a plurality of different types of body interface devices 14, such as a female urinal, a male condom, a urostomy body fitment, or a catheter.

The liquid sensor 18 may be held in an operative position within the sensor recess 36 by one or more of a variety of possible arrangements, for example, a peelable adhesive, or a peelable mechanical fastener, such as Velcro (or other hook-loop or hook-hook material), or a mechanical coupling based on interference fitting, or other mechanical means.

In another form, the liquid sensor 18 may not intended to be separated from the body interface device 14, and may be permanently attached to, or integrated with, the cover 24. A permanent attachment may, for example, be effected by one or more of a permanent adhesive, welding, or a mechanical coupling.

The liquid sensor 18 can take a variety of different forms. Optionally, the liquid sensor 18 is selected from: a capacitance sensor; an ultrasonic sensor; a piezo-electric (or piezo-resonant) sensor; a temperature sensor; and an electro-optic sensor. At least the wall portion 32a of the housing portion 32 has suitable properties that permit detection of liquid through the material of the wall portion 32a, depending on the type of sensor 18 used. Typically, the wall portion 32a is suitably thin to permit liquid detection with a desired sensitivity, and yet is thick enough to optimize the signal-to-noise ratio.

A capacitance sensor detects proximity of liquid according to changes in the dielectric effect of liquid proximity, compared to air proximity. The dielectric effect affects the electric field in the active zone around the sensor, and thus, the effective capacitance in the sensor. The capacitance is monitored by any suitable capacitance sensing circuit (not shown), such as an RC oscillator whose oscillation frequency and/or whether oscillation occurs, is dependent on the value of a resistor in combination with the effective capacitance of the sensor. The oscillation in turn triggers an output stage, coupled to an output amplifier, to generate an output signal indicative of liquid presence. The capacitance sensing circuit is preferably disposed near or at the liquid sensor 18 (e.g., as part of the liquid sensor 18 itself), or the capacitance sensing circuit can be disposed at the aspiration unit 12, or at a point along electrical connector 19. A suitable capacitance sensor and capacitance sensing circuit are described in U.S. Pat. No. 5,576,619, the contents of which are hereby incorporated by reference.

The invention has been tested using a capacitance "smart" sensor from SIE Sensors. The sensor 18 of dimension 35 mm (length)×22 mm (width)×10 mm (height) was affixed to the external wall of a body interface device 14. The sensor 18 detected the presence of two test liquids, water and saline solution, as soon as the liquid was introduced, and provided an activation signal to the aspiration unit 12 within milliseconds. The electric field from the sensor 18 is able to penetrate a wide variety of plastic components (e.g., polyethylene (PE), polypropylene (PP) and acrylics), either transparent or opaque, with great sensitivity.

An ultrasonic sensor works using the principle of sonar at the ultrasonic frequency range. A transducer is resonated at a set frequency to convert electric energy into ultrasonic frequency range acoustic energy. The ultrasonic acoustic waves are emitted towards a liquid collection region. Energy is reflected either from the walls if the region is empty of liquid, or from liquid if present in the region. By measuring the time delay for reflected waves to arrive, and comparing this to one or more pre-calibrated time delays taken when the liquid collection region is empty, the presence of liquid can be reliably and quickly detected. An example of ultrasonic liquid sensor is described in U.S. Pat. No. 3,960,007, the content of which is incorporated herein by reference. A commercially available ultrasonic sensor is made available by ZEVEX Inc.

A piezo-electric or piezo-resonant sensor also uses high frequency, e.g., ultrasonic energy or acoustic signal, in a similar way to the ultrasonic sensor described above. The ultrasonic or acoustic signal could penetrate either transparent or opaque plastic walls. An example of piezo-electric sensor is described in U.S. Pat. No. 3,948,098, the content of which is incorporated herein by reference.

The invention has been tested with a piezo-resonant sensor obtained from GEMS Sensors. The sensor 18 of diameter 40 mm was attached to the external wall of the body interface device 14 in the receiving chamber 34, and detected the presence of liquid as soon as introduced.

The sensor 18 may alternatively be an electro-optical sensor. In such a case, at least the wall portion 32a is made of material that is transparent to the optical radiation used by the electro-optical sensor. For example, the optical radiation may be in the infra-red range, and/or the visible range, and/or ultra-violet range. The term "optical" as used herein means that the radiation lies in a frequency range that obeys substantially the laws of optics. The electro-optical sensor comprises an electro-optical emitter, an electro-optical receiver, and sensing circuitry for detecting the presence of liquid according to the electrical output of the electro-optical receiver. The sensing circuitry is preferably disposed at the liquid sensor 18 (e.g., as part of the liquid sensor 18), or the sensing circuitry is disposed at the aspiration unit 12, or at a point along electrical connector 19. An example electro-optical liquid sensor is described in U.S. Pat. No. 4,354,180, the content of which is incorporated herein by reference.

Alternatively, a temperature sensor may be used as the liquid sensor 18. At least the wall portion 32a is of a material allowing the temperature sensor 18 to be exposed to an increase in temperature should upon urine discharge. At the same time, the wall portion 32a prevents the sensor 18 from coming into physical contact with the liquid. The wall portion 32a may be made of a heat conductive material, or it may be made of other material that is thin enough (e.g., a film) so as not to provide substantial heat insulation. The use of a temperature sensor 18 can provide a reliable and quick indication of body liquid exiting the body, without requiring the sensor to be dispersed over a large area. Urine, exits the body at a temperature of about 37° C., which is notably higher than ambient room temperature (typically about 23° C.), and also higher than the ambient temperature of a sensor positioned close to the human skin (typically about 32° C.).

The presence of liquid may be detected by detecting (i) a rapid change in temperature, such as an increase of 1° C. within two seconds and/or (ii) a temperature rise above a threshold, such as above 36° C.

In all of the above forms, the liquid sensor 18 generates an electrical output signal responsive to proximity of detected liquid. The electrical signal is communicated to the aspiration unit 12 by means of an electrical connector 19. The feature of the liquid sensor 18 being coupled to the aspiration unit 12 by an electrical connector 19 avoids the expense and fragility associated with using an optical fiber connection. The electrical connector 19 may be integrated with, or separate from, the flexible conduit 16. The electrical connector 19 also supplies power from the aspiration unit 12 if needed to power the liquid sensor 18, or to power active circuitry within the liquid sensor 18. The housing portion 34 optionally includes a channel recess 19a for accommodating the electrical connector 19 where the connector 19 exits the sensor 18.

Referring back to FIG. 1, the aspiration unit 12 comprises a power supply 40, an electronic control unit 42, and a suction source 44. The power supply 40 is selected as one or more of: a replaceable battery, a rechargeable battery, radiation collection panels, and a mains power supply. Preferably, the power supply 40 includes a combination of a rechargeable battery and a mains power supply; such a combination allows portable operation when the aspiration system 10 is not connected to a mains power supply, as well as automatic recharging of the battery when the aspiration system 10 is coupled to a mains power supply. Additionally or alternatively, the power supply 40 includes radiation collection panels, such as photovoltaic panels or cells for generating electricity from ambient light, which can improve autonomy of operation or for charging the rechargeable battery. The power supply 40 provides power for the electronic control unit 42, the liquid sensor 18 (if needed), and any power needed by the suction source 44. The electronic control unit 42 and the liquid sensor 18 could have a separate power supply from the suction source 44. In the present embodiment, the suction source 44 is an electric pump 44a that operates under control of the electronic control unit 42, responsive to detection of liquid by the liquid sensor 18. The pump 44a could be a suction device based on diaphragm, peristaltic, volume displacement, spring, gravity, siphon, heat-recoverable metal drive, or an in-line pump. The flexible conduit 16 is coupled through the pump 44a to a liquid collection chamber 46. The liquid collection chamber 46 may either be separate from the aspiration unit 12 and coupled thereto with a suitable connector, or the liquid collection chamber 46 may be integral with and/or housed in the aspiration unit 12.

When the liquid sensor 18 indicates that no liquid is detected, the control unit 42 controls the pump 44a in a quiescent state. Either the pump 44*a* is deactivated to generate no suction, or the pump 44*a* is operated periodically or at a slow speed to produce low suction (which may encourage the body interface device 14 to hug against the skin, and produce a better seal against the skin).

When the liquid sensor 18 detects the presence of discharged liquid, the control unit 42 activates the pump 44*a* to generate suction through the flexible conduit 16 to draw the liquid from the body interface device 14 into the liquid collection chamber 46. The control unit 42 may operate the pump 44*a* for as long as liquid continues to be detected by the liquid sensor 18, or for a predetermined time interval after liquid detection has finished. Once collected by the liquid collection chamber 46, the volume of liquid output may be measured, or the liquid may be inspected visually, or sent for biochemical testing or analysis.

In an alternative form, instead of a pump 44*a* directly applying suction to the flexible conduit 16, the suction source 44 may comprise a vacuum chamber charged with a low pressure vacuum, and an electronically controlled valve for controlling application of suction from the vacuum chamber to the flexible conduit 16. A pump may be provided for charging the vacuum chamber with the vacuum.

When it is desired to replace the body interface device 14, either for the same patient or for fitting to a new patient, the liquid sensor 18 may be separated from a current body interface device 14. The current body interface device 14 is disposed of, and the same liquid sensor 18 is available to be used with a replacement body interface device 14. In the case where the non-contact liquid sensor is permanently attached to the body interface device 14, a quick connector along electrical connector 19 and flexible conduit 16 is equipped to allow for the replacement of body interface device 14.

It will be appreciated that the body interface device 14 of the preferred embodiments can be comfortable to wear, be discrete without bulging significantly under undergarments, and yet also provide a reliable seal around the genital region to prevent overspillage and leakage of discharged urine. In particular, the embodiments address the difficulties associated with such a device for female wearers.

Moreover, the aspiration system 10 as described herein provides significant advantages compared to the prior art, and can address or mitigate many of the drawbacks of the prior art, especially in terms of efficient detection of liquid without electrical contact with the body liquid. The disposability of the body interface device 14, and optional reusability of the liquid sensor 18 without contact with the discharged liquid, make the aspiration system 10 very hygienic and cost efficient. The aspiration system 10 is also extremely versatile, and a single aspiration system 10 or different embodiments can have a wide variety of applications. For example, the invention is usable in acute care, home care, and long term care situations or facilities. The invention is usable with wheelchairs, and with bed-bound patients, as well as being able to be implemented as a fully portable device. The invention enables the aspiration system 10 to be discrete, thereby preserving the patient's dignity and privacy. The invention may also be used with catheters, either for detecting liquid (urine) presence in a catheter, or for collecting urine from a short catheter that projects a short distance from the body into the body interface device 14.

It will be appreciated that many modifications, improvements and equivalents may be made within the claimed scope of the invention.

We claim:

1. A body interface device for a urine aspiration system, the body interface device comprising:

an adhesive skin contact pad for adhering to skin, the pad including at least one aperture for admitting urine through the pad into the body interface device; and a cover attached to the pad and having a bulged form projecting away from the pad, the cover defining (i) a liquid collection chamber region facing towards the pad for receiving discharged urine, and (ii) a recess for receiving at least partly a non-contact liquid sensor outside the liquid collection chamber region, the liquid collection chamber portion and the recess being adjacent to each other and separated by a wall portion in common to the liquid collection chamber region and the recess.

2. The body interface device of claim 1, wherein the recess is defined by a pocket in the bulged form.

3. The body interface device of claim 1, wherein the liquid collection chamber region overlaps at least partly the recess in a depth direction generally perpendicular to the adhesive pad.

4. The body interface device of claim 1, wherein the wall portion has a cup or well shape.

5. The body interface device claim 1, wherein the bulged form of the cover defines a profile height in a depth direction of the device, and wherein the wall portion is spaced from the adhesive pad by a distance less than the profile height.

6. The body interface device of claim 1, wherein the recess has a depth less than the depth of the chamber at the deepest part of the chamber.

7. The body interface device of claim 1, wherein the recess is nested within the periphery of the chamber.

8. The body interface device of claim 1, wherein the cover further comprises a flange portion in face to face contact with at least a peripheral region of the adhesive pad.

9. The body interface device of claim 1, wherein the adhesive pad extends at least partly over a mouth of the chamber.

10. The body interface device of claim 1, wherein the cover further comprises a urine outlet port communicating with the chamber, for aspiration of urine therethrough.

11. The body interface device of claim 1, wherein the cover is flexible.

12. The body interface device of claim 11, wherein the flexible cover has a thermo-formed shape.

13. The body interface device of claim 11, wherein the flexible cover is made of one or more polyolefins.

14. The body interface device claim 1, wherein the adhesive pad comprises or carries gel adhesive for adhering to the skin.

15. The body interface device of claim 14, wherein the gel adhesive comprises one or more materials selected from: a thermoplastic elastomer; polyurethane; hydrogel; silicone; acrylic; hydrocolloid.

16. The body interface device of claim 14, wherein the gel adhesive has one or more of the following adhesion properties: (i) a tack of at least 300 grams; (ii) an adhesive strength of at least 0.2 N/in.; (iii) a peel strength of not more than 3 N/in.

17. The body interface device of claim 14, wherein the gel adhesive has a thickness selected from: (i) at least 2 mils; (ii) at least 20 mils.

18. The body interface device of claim 14, further comprising a liquid acquisition material disposed within the liquid collection chamber region, for acquiring urine discharged into the body interface device, and distributing urine adjacent to the wall portion.

19. The body interface device of claim 18, wherein the liquid acquisition material has one or more of the following liquid handling properties: (i) a wicking characteristic for wicking urine; (ii) hydrophobic.

20. The body interface device of claim 18, wherein the liquid acquisition material comprises one or more selected from: bonded PET fiber fleece; needled punched non-woven; cellulose fibers.

21. The body interface device of claim 1, further comprising a non-contact liquid sensor received or receivable within the recess, for sensing through said wall portion the presence of urine within the first chamber.

22. The body interface device of claim 21, wherein the non-contact liquid sensor is separable from the cover.

23. The body interface device of claim 21, wherein the non-contact liquid sensor is permanently attached to the cover.

24. The body interface device of claim 21, wherein the non-contact liquid sensor is a sensor selected from: a capacitance sensor; an ultrasonic sensor; a piezo-electric sensor; a piezo-resonant sensor; a temperature sensor; an electro-optic sensor.

25. The body interface device of claim 1, wherein the adhesive pad and the cover are shaped for fitting a female's genital area.

26. The body interface device of claim 25, wherein the adhesive pad has a shape selected from: a pear shape; a boat shape with enlarged ends.

27. A body interface device for a urine aspiration system, the body interface device comprising:

a skin contact pad comprising or carrying gel adhesive for adhering to skin; a gasket including at least one aperture for admitting urine through the gasket into the body interface device; and a flexible cover attached to the gasket and having a bulged form projecting away from the gasket, the flexible cover defining a liquid collection chamber region facing towards the gasket for receiving urine and a recess for receiving at least partly a non-contact liquid sensor outside the liquid collection chamber region.

28. A body interface device for a urine aspiration system, the body interface device comprising:

a cover defining a liquid collection chamber region for receiving urine discharged into the device, the liquid collection chamber region including a trough region extending at least partly around an island or peninsular region of the cover;

a non-contact liquid sensor disposed within said island or peninsular region of the cover in non-contact relation with the liquid collection chamber region; and a liquid acquisition material in the liquid collection chamber region for acquiring urine entering the liquid collection chamber collection region, and for transporting the urine adjacent the island or peninsular region for sensing by the non-contact liquid sensor.

29. The body interface device according claim 28, wherein the body interface device is configured to seal against the female genital area.

* * * * *